United States Patent [19]

Haseltine et al.

[11] Patent Number: 5,043,262
[45] Date of Patent: Aug. 27, 1991

[54] PROTEIN, SEQUENCES CONTAINING THE VPU GENE THEREFORE, VECTORS, METHODS OF PREPARATION AND USE

[75] Inventors: William A. Haseltine, Cambridge; Ernest Terwilliger, Boston; Eric Cohen, Brighton, all of Mass.

[73] Assignee: Dana Farber Cancer Institute, Boston, Mass.

[21] Appl. No.: 193,321

[22] Filed: May 12, 1988

[51] Int. Cl.$^5$ .................. C07K 15/04; C12Q 1/70; G01N 33/569

[52] U.S. Cl. ........................... 435/5; 530/350; 435/7.2

[58] Field of Search .............. 530/350; 514/12; 435/7, 435/69.1, 69.3, 172.1, 320, 5, 7.2, 320

[56] References Cited

PUBLICATIONS

Strebol, Science (Sep. 2, 1988), 241:1221-1223.

Primary Examiner—Howard E. Schain
Assistant Examiner—K. Keith Baker
Attorney, Agent, or Firm—David G. Conlin; Ronald I. Eisenstein

[57] ABSTRACT

A protein having molecular weight of approximately 16 kD which is also cleaved into a protein having a molecular weight of 15 kD is disclosed. This protein is referred to as viral protein U and produced by the vpu gene. It is disclosed that this protein has antigenic determinants and can be used to screen for people having the HIV-1 virus.

15 Claims, 8 Drawing Sheets

FIG. 1B

```
                                                    PEPTIDE #1
       1        10 11      20 21      30 31      40 41      50
U ELI  MQPLGIIAIA ALVVAIILAI VVWTIVFIEY RRIKKQRRID CLLDRITERA
UHXB2  T**IP*V**V ********I** ****S***I** *K*LR***K** R*I***LI***
UBH10  M**IQ*-**V ********I** ****K***I** *K*LR***K** R*I***LI***
UBH8   M**IP*VT*V A*I **K*I** *K*LR*K R*I*LI*
UHXB3  M**IQ*-**V ********I** ****K***I** *K*LR***K** R*I***LI***
UMAL   I***V*L**V ****TL*I** ****K***I** *K*RR***K** R*I***IR***
UBRU   M**IQ*-*** ********I** ****K***I** *K*LR***K** R*I***LI***
USF2   M*S*Q*LV S**VA*I *L* *K*LR***K[I]* R*I****R*K*

PEPTIDE #2
       51       60 61      70 71      80 81 85
U ELI  EDSGNESEGD REKLSKL--- -VEMGHHAPW DIDDL  •     (81)
UHXB2  ********** ---I*A*VEM G*********  *V***  •    (82)
UBH10  ********** ---I*A*VEM G*********  *V***  •    (81)
UBH8   ********** ---I*A*VEM G*********  *V***  •    (82)
UHXB3  ********** ---I*A*VEM G*********  *V***  •    (81)
UMAL   ********** TEE*****-- -*****D***  *V***  •    (81)
UBRU   ********E* ---I*A*VEM G*********  *I***  •    (80)
USF2   QEEK*A*VEM G---*L****  *V***  •                (82)
```

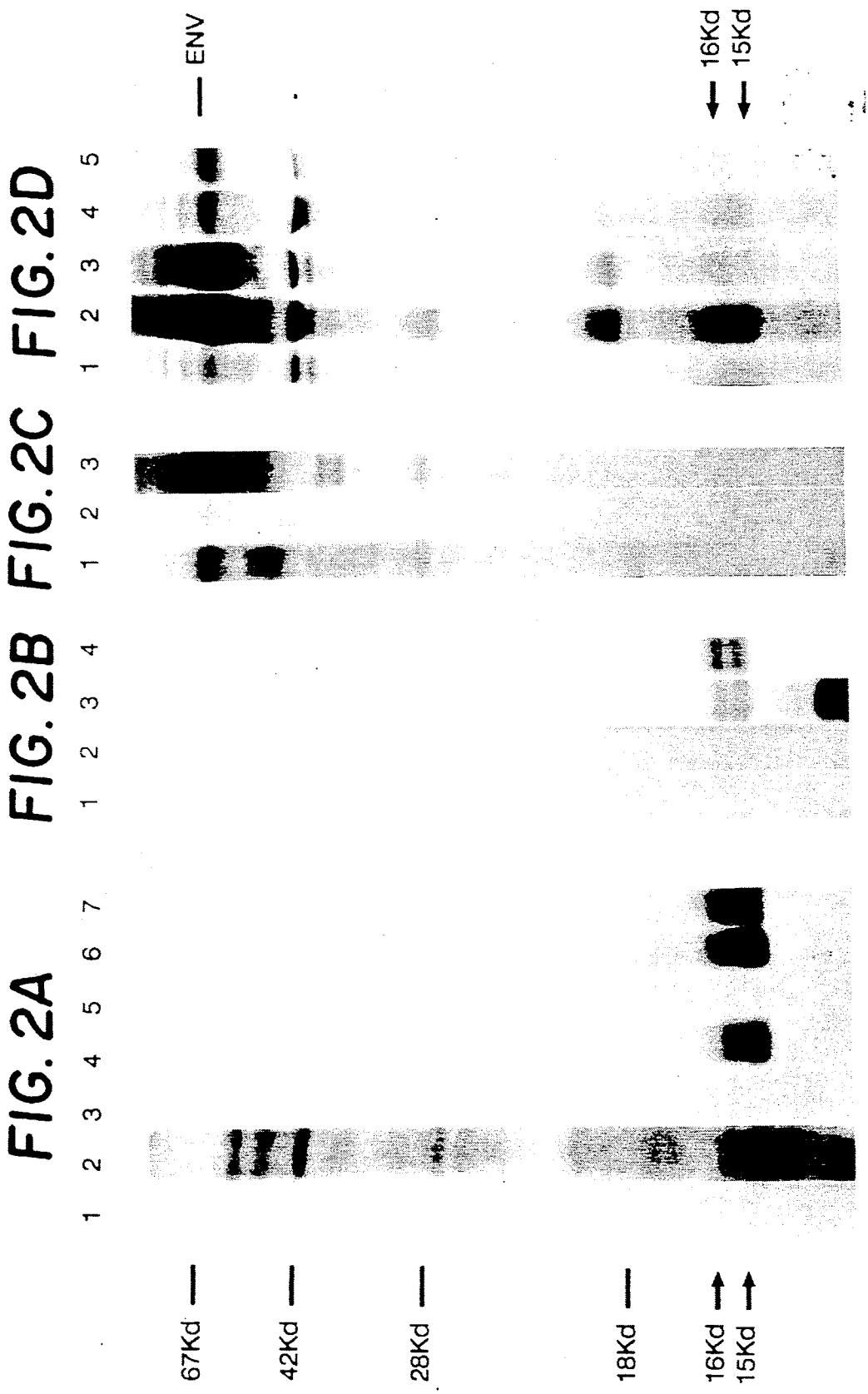

PROTEIN, SEQUENCES CONTAINING THE VPU GENE THEREFORE, VECTORS, METHODS OF PREPARATION AND USE

The present invention is directed to a new purified polypeptide, a method of producing this polypeptide, an antibody to this protein, an assay for detecting in biological specimens the presence of an antibody to the antigenic determinants present in said polypeptide, and an assay for the negative effect of this protein upon viral replication.

The human immunodeficiency virus (HIV-I, also referred to as HTLV-III, LAV or HTLV-III/LAV) is the etiological agent of the acquired immune deficiency syndrome (AIDS) and related disorders. [Barre-Sinoussi, et al., *Science* 220:868-871 (1983); Gallo et al, *Science* 224:500-503 (1984); Lane et al, Levy et al, *Science* 225:840-842 (1984); Popovic et al, *Science* 224:497-500 (1984); Sarngadharan et al, *Science* 224:506-508 (1984); Siegal et al, *N. Encl. J. Med.* 305:1439-1444 (1981)]. This disease is characterized by a long asymptomatic period followed by the progressive degeneration of the immune system and the central nervous system. Studies of the virus indicate that replication is highly regulated, and both latent and lytic infection of the CD4 positive helper subset of T-lymphocytes occur in tissue culture. [Zagury et al, *Science* 231:850-853 (1986)]. The expression of the virus in infected patients also appears to be regulated as the titer of infectious virus remains low throughout the course of the disease. Molecular studies of the replication and genomic organization of HIV-I show that it encodes at least eight genes [Ratner et al, *Nature* 313:277-284 (1985); Sanchez-Pescador et al, *Science* 227:484-492 (1985); Muesing et al, *Nature* 313:450-457 (1985); Wain-Hobson et al, *Cell* 40:9-17 (1985)]. Three of the genes, the gag, pol and env genes are common to all retroviruses. However, the genome also encodes five additional genes that are not common to most retrovirus, the sor, tat, art and 3'orf and R genes [Sodroski et al, *Science* 221:1549-1553 (1986); Arya et al, *Science* 229:69-73 (1985); Sodroski et al, *Science* 227:171-173 (1985); Sodroski et al, *Nature* 321:412-417 (1986); Feinberg et al, *Cell* 46:807-817 (1986); Wong-Staal et al, *AIDS Res. and Human Retroviruses* 3:33-39 (1987), which are all incorporated herein by reference.]

Nucleotide sequences from viral genomes of other retroviruses namely HIV-II and Simian immunodeficiency virus (SIV) (previously referred to as STLV-III) also contain tat and art regulatory sequences and show transactivation in addition to containing the structural genes. [Guyader et al, *Nature* 326:662-669 (1987); Chakrabarti et al, *Nature* 328:543-547 (1987)]. It would be useful to have a method for readily distinguishing between HIV-I and other retroviruses, such as HIV-II.

One of the problems with developing a vaccine to the AIDS virus is that the various strains of HIV are not highly conserved. And, the envelope protein, which has been used as a target because it goes to the surface of the cell, shows a great deal of variability between strains. Accordingly, it would be useful if there was another protein that went to the surface of the cell and was highly conserved in different HIV strains.

Any HIV product which demonstrates a negative effect upon virus replication requires evaluation for possible therapeutic applications. Specifically, an assay for the negative effect is required so that drugs can be evaluated for possible usefulness as agents to enhance or mimic the negative effect.

SUMMARY OF INVENTION

We have now discovered a protein expressed by cells infected with HIV-I. The protein has a molecular weight of approximately 16 kD, but is cleaved to a 15 kD form. This protein has antigenic determinants and patient antisera from AIDS infected patients recognize both forms of this protein whereas the antisera of normal patients do not recognize it.

This protein appears to have a negative effect upon the replication of the HIV-1 virus in cultured human CD4+ lymphocytes.

BRIEF DESCRIPTION OF DRAWINGS

FIG. 1B shows the alignment of the vpu gene protein sequence.

FIG. 2A-D are radiograms showing the in vitro characterization of the vpu gene product.

DESCRIPTION OF INVENTION

We have now discovered that HIV-1 encodes an additional protein and that antibodies to this protein are detected in the sera of people infected with HIV-1. Further, this protein can be used to distinguish HIV-1 isolates from the other human and simian immunodeficiency viruses (HIV-2 and SIV) [Guyader, M., et al, *Nature* 326, supra (1987)]; Hirsch, V., et al, *Cell* 49:307-319 (1987); Chakrabarti, L, et al *Nature* 328, supra] since we have also discovered that the latter viruses do not encode a similar protein.

Figure 1A:
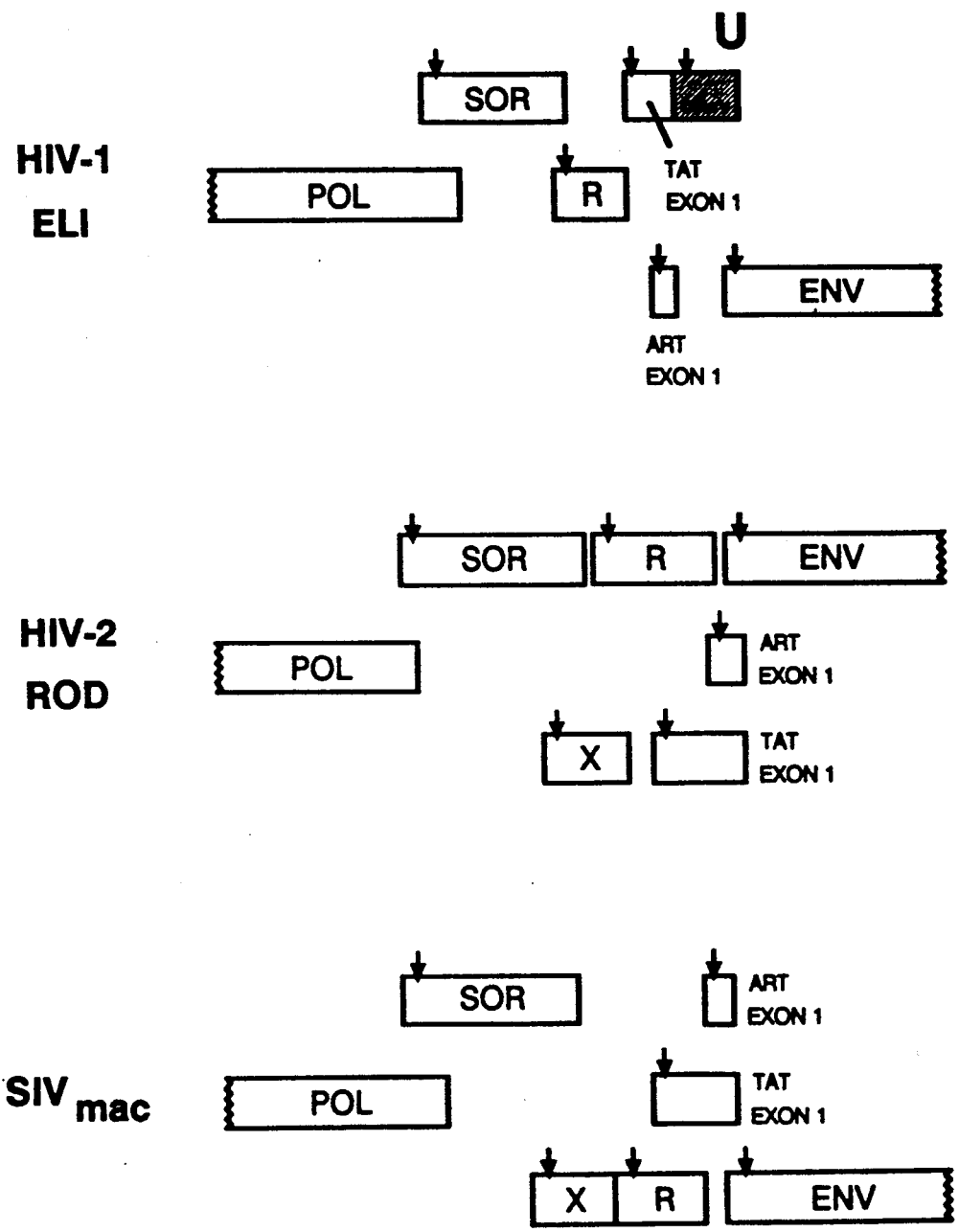
FIG. 1A shows the genetic organization of the central region of the Eli strain of HIV-1 compared to SIV and the ROD strain of HIV-2.

This protein is expressed by a DNA segment containing a sufficient number of nucleotides corresponding to nucleotides 5541-8017 of the HIV-1 genome, where an AUG codon is inserted immediately upstream and in the proper reading frame with this region to express a polypeptide. This region typically corresponds to the U open reading frame. A schematic diagram of this open reading frame from the region between the first coding exons of the tat and art genes of HIV-1 and the envelope glycoprotein gene is pictured in FIG. 1A. However, many strains do not contain an AUG codon in the proper reading frame. The Eli strain of HIV-1 does contain such an arrangment. FIG. 1A shows the genetic organization of the central region of HIV-1 (Eli isolate, 24) compared to SIV (20,21) and HIV-2 (ROD isolate, 19). Arrows indicate the initiator AUG codons in the viral genes. Many HIV-1 strains have the capacity to encode this protein which is about 80 to 82 amino acids long and synthesized from this region when initiated with an AUG codon. FIG. 1B illustrates alignment of this protein sequence among various strains The Eli strain is taken as reference. Gaps (—) were introduced using standard methodology to optimize the alignment. Asterisks indicate amino acid identity. The HIV isolates compared include Eli, Mal [Alizon, M., et al, *Cell* 46:63–74 (1986)]. HXBc2, BH-10, BH-8, pHXB3 [Ratner, L., et al, *Nature* 313:277–283 (1985)], BRU [Wain-Hobson, S., et al, *Cell* 40:9–17 (1985)] and USF2 ]Sanchez-Pescador, R., et al, *Science* 227:484–492 (1985)]. ]All of the above-mentioned references are incorporated herein by reference]. These strains are generally available. USF2 contains a termination codon at position 39, however, a - 1 point frameshift results in a protein 43 amino acids longer that is well conserved when compared with the Eli reference sequence. This new protein contains a hydrophobic leader sequence (FIG. 1C), which resembles membrane transport sequences.

This suggests that the protein is transported across the cell membrane. Further, the position of the U reading frame within the viral genome suggests that the protein forms an alternate leader sequence for the envelope glycoprotein. Occurence of either a splicing event or a frameshift in translation of the U protein at position X would result in the production of a fusion protein with the envelope glycoprotein. In such a case, the U protein would become attached to the amino terminal of the envelope glycoprotein forming a new amino terminal.

The protein, which has a molecular weight of about 16 kilodaltons (kD) can be cleaved to yield a shorter form of the protein, which has a molecular weight of about 15 kD.

Because the gene for this protein is located in an open reading frame that has been designated U [Wain-Hobson, S. et al, *Cell* 40:9–17 (1985)] we propose calling the viral protein U and the gene vpu for viral protein U.

Figure 1C:
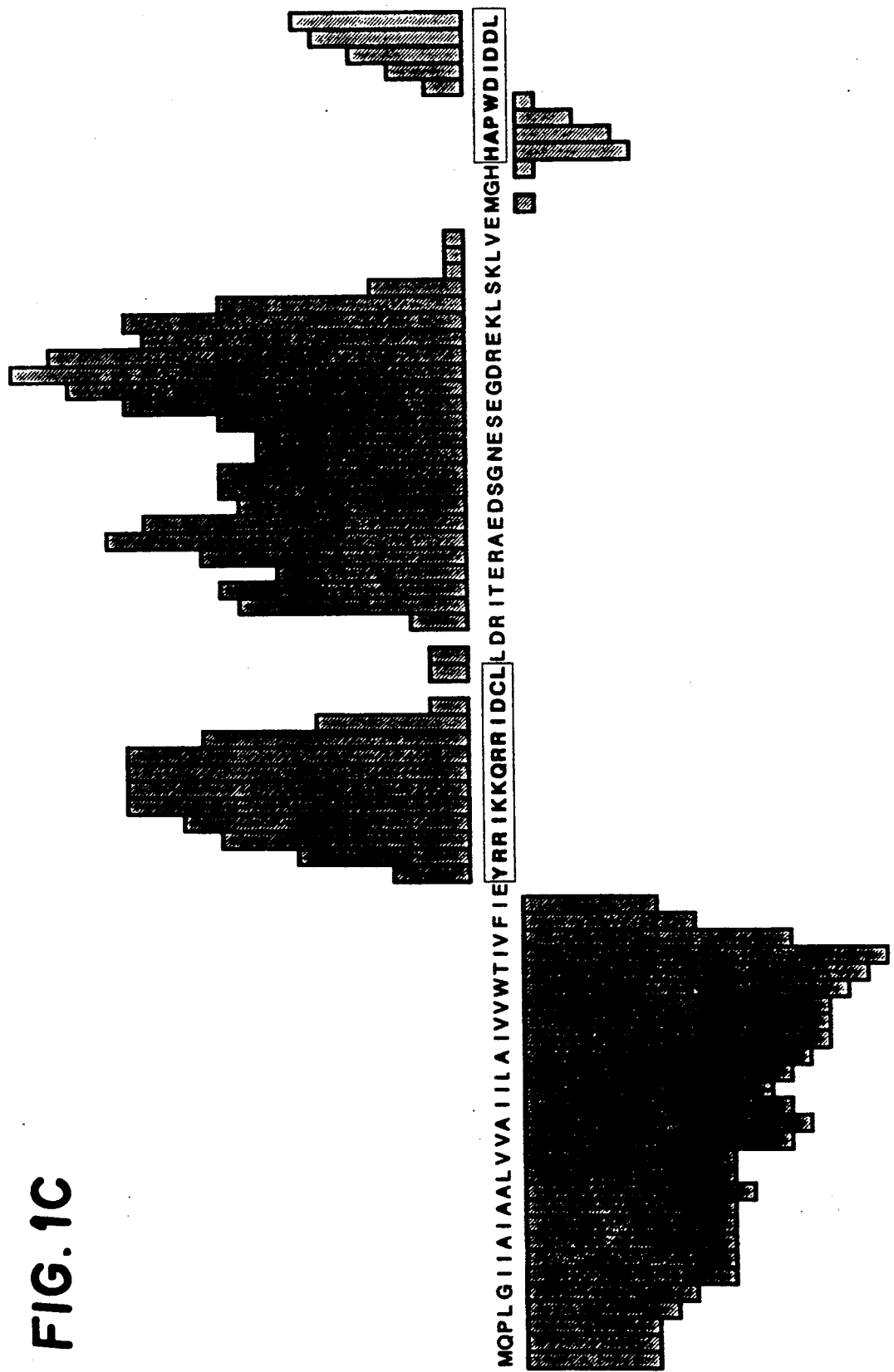
FIG. 1C is a hydrophobic profile of the predicted vpu gene product.

In order to more fully examine the properties of this protein, two oligopeptides were made corresponding in sequence to the hydrophilic regions of the protein based upon amino acid sequence composition. The first oligopeptide designated peptide 1, corresponded to amino acids 29–41, while the second oligopeptide designated peptide 2, corresponded to amino acids 73–81 (FIGS. 1B, 1C). These peptides were conjugated to keyhole limpet hemocyanin using standard techniques and were used to raise antibody in a number, for example, 3 rabbits. After multiple injections of the antigen, the rabbits did produce antibodies that recognize the immunizing oligopeptide.

FIG. 2 shows the in vitro characterization of the vpu gene product. Both, the 15 kD and 16 kD viral proteins were precipitated by the rabbit antiserum to peptide 2 (see FIG. 2A, lane 4). The antisera to peptide 1 also precipitated these proteins, although more weakly. In contrast, these proteins were not precipitated by the sera from preimmune rabbit sera (FIG. 2A, lane 3). The data of FIG. 2D demonstrates that HIV seropositive patient antiserum also recognize both the 15 kD and 16 kD proteins (lane 2). This ability of the patient antisera to precipitate the two proteins is partially competed by peptide 2 (See lane 3). All of the 19 sera of HIV-1 infected patients that immunoprecipitated the truncated envelope product were also found to precipitate both the 15 kD and 16 kD proteins. These proteins were not recognized by normal patient antiserum (lane 1).

This protein appears to be highly conserved among HIV-1 proviral strains. Indeed, all HIV-1 proviral strains isolated contain an open reading frame in the region corresponding to vpu. However, many individual proviral strains explored in vitro appear unable to produce a protein from this region because of a single point mutation that prevent vpu expression. Indeed, different proviral strains isolated from the same virus isolate are heterogeneous with respect to the ability to encode vpu. For example, independent proviral clones of the IIIB isolate HXBc2, BH10, BH-8 and BH-3 differ in this regard (See FIG. 1B). A similar variation in the ability of individual proviral clones to encode other viral protein, especially the 3' orf product, has also been noted. For example, in the case of the isolate of IIIB with respect to 3'orf, a mutation that truncates the protein product yields a virus that replicates more rapidly in culture than does the wild type [Terwilliger, E. et al, *J. Virol.* 60:754–760 (1986)]. Proviruses incapable of expressing vpu can replicate, as is demonstrated by the ability of the virus produced by transfection with, for example, the provirus HXBc2 to grow in T-cells in culture, although this is a vpu-deficient viruses. This, however, does not rule out the possibility that the vpu product plays an important role in regulation of viral replication or pathogenesis.

Indeed, a computer assisted search for proteins similar to p15$^{vpu}$ and p16$^{vpu}$ found that HIV-2 and SIV do not encode a similar protein. Neither strain contained an open reading frame comparable to the U reading frame. Both HIV-2 and SIV strains contain an open reading frame missing from that of HIV-1 isolates, the X open reading frame [Guyader, M. et al, *Nature* 326, supra (1987)] but there is no detectable similarity in the vpu protein and any protein that could be formed from the X open reading frame. Furthermore, none of the sera of HIV-2-infected patients surveyed contained antibodies to the vpu product nor were antibodies to the vpu product detected in *Rhesus macaques* infected with SIV.

Thus, antisera to p15$^{vpu}$ and p16$^{vpu}$ can be used to distinguish among HIV-1 and SIV or HIV-2 infections.

Additionally, the titer of patient antibodies to the vpu product can also be used to determine the stage of HIV-1 induced disease. By examining the viral messenger RNAs that are used to encode regulatory proteins [Meusing, M. A., et al, *Nature* 313:450–458 (1985), Arya, S. K., et al, *Science* 229:69–73 (1985) and Sodroski, J. et al, *Nature* 321:413–417 (1986)] it is apparent that vpu is removed by splicing from such viral mRNAs. Accordingly, vpu should not be made in the absence of the art gene product as only fully spliced mRNAs accumulate in the absence of this product. [Sodroski, *Nature* 321, supra: Feinberg, M. B., et al, *Cell* 46, supra (1986)]. Consequently, the vpu protein is, like other virion proteins, synthesized late in infection, and the titer of patient antibodies can be used to determine the stage of the disease.

Expression of the U protein can readily be carried out by the person of ordinary skill in the art by using standard techniques based upon the present disclosure. For example, one can prepare a DNA segment containing the vpu gene, a nucleotide sequence corresponding to a sufficient number of nucleotides from nucleotides 5541–8017, where an AUG codon is inserted immediately upstream and in proper reading frame with this region to express the U protein. Typically, this DNA segment will be inserted into a vector which contains a promoter, preferably a viral promoter, upstream of the segment. The vector preferably also contains an enhancer and polyadenylation signal. Preferably, one would use the nucleotide sequence corresponding to the U open reading frame in the HIV provirus, however, when using a strain that does not contain an AUG initiation codon such as HXBc2, care must be taken to insure that the initiator sequence AUG is added in the proper reading frame such as occurs in HIV strain Eli. Accordingly, the use of a sequence corresponding to the U open reading frame is most preferable.

If one was to use a strain corresponding to the U open reading frame from for example, strain HXBc2, one would have to insert an AUG codon immediately upstream and in proper reading frame with the U open reading frame at a nucleotide corresponding to immediately before nucleotide sequence 5541 or create a point mutation to generate such a sequence. However, this can be done by standard techniques well known in the art.

Figure 4:
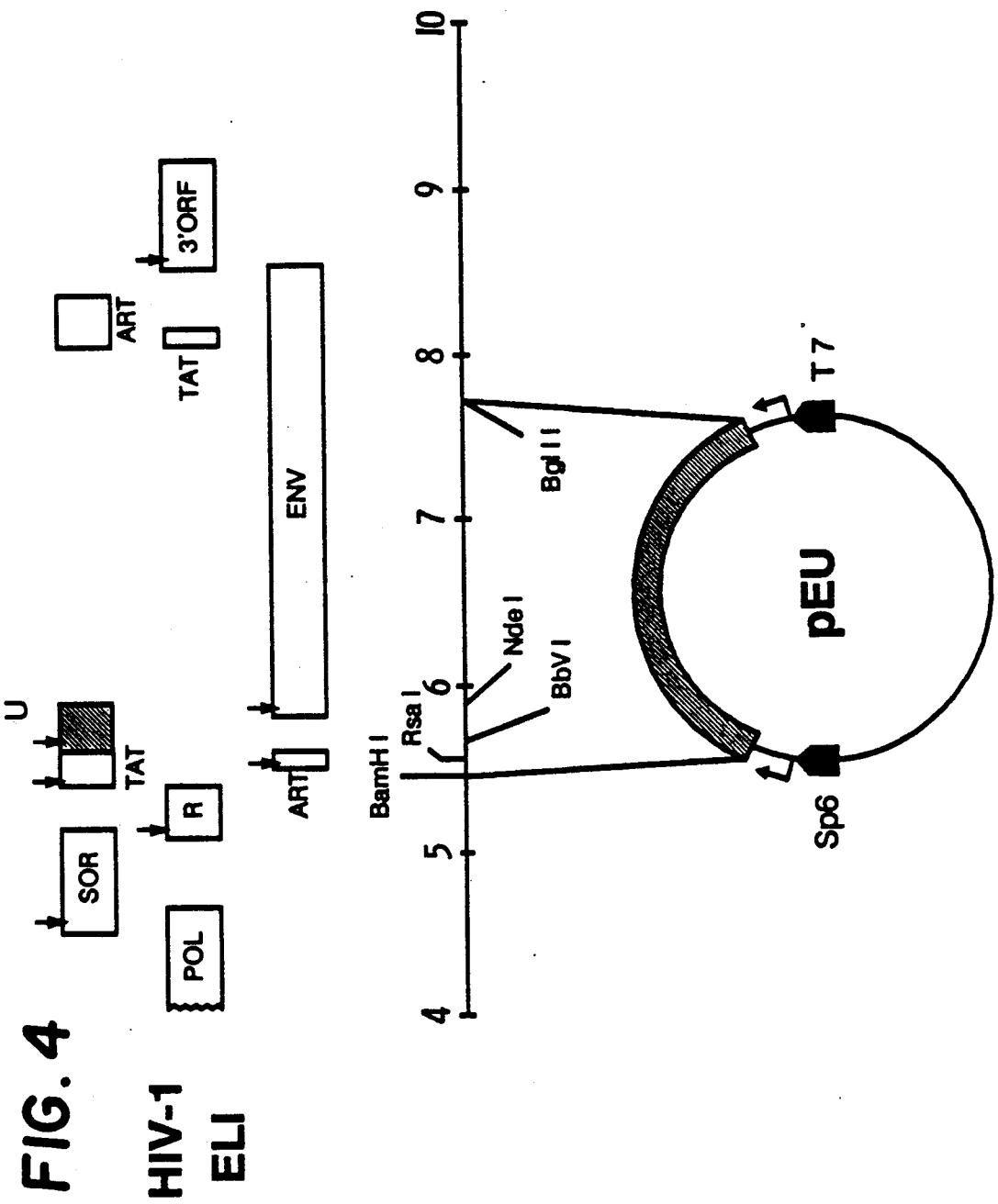
FIG. 4 is a schematic showing the plasmid pEU used to synthesize messenger RNA.

By inserting a vpu gene in a standard expression vector, for example, the SP6 plasmid, using techniques well known in the art. (See FIG. 4 showing creation of plasmid pEU), this plasmid can be used to synthesize the p15$^{vpu}$ and p16$^{vpu}$ by standard techniques.

This protein can be used in preparing an antigen to create a vaccine, for example, a live attenuated vaccine. By using this protein it is possible to generate an antigenic response to the protein and because of the aforesaid properties that the protein is found on the surface of cells infected by the virus and because this protein appears to be highly concerned among various HIV-1 strains, the vaccine created should be particularly useful.

As mentioned above, because it contains antigenic determinants, which are highly conserved, and appear to be specific to cells infected with HIV-1 this protein is particularly useful as a diagnostic tool for assaying biological specimens to determine whether they contain cells which have been infected with HIV-1. These assays can be prepared using standard techniques. For example, one can take a predetermined sample, i.e., the biological specimen to be tested, and add an anti-idiotypic antibody or immunologically similar to the antigenic sites of the p15$^{vpu}$ and p16$^{vpu}$. For example, peptide 2 described herein, corresponding to amino acids 73-81 (FIGS. 1B, 1C), reflects such an antigenic site. One can preferably use monoclonal anti-idiotypic antibodies. This sample is then screened to determine if there is a reaction, i.e. if a complex is formed between antibody and antigen. Alternatively, one can assay with antibodies either monoclonal or polyvalent to the antigenic determinants of the viral protein itself using known immunoassay methods, for example, using competitive immunoassays or immunometric (sandwich) assays.

Because this protein appears to have an attenuating effect upon the rate of spread of an HIV-1 infection in culture, it may form the foundation for a screening program of drugs or other agents designed to mimic or enhance this phenomenon. For example, one can add the protein to a culture infected with an HIV-1 strain that does not express the protein, measure the degree of attenuation of replication, then screen for drugs that enhance this attenuation effect by standard techniques. The protein can be added by any technique well known in the art including transfecting the cells with an expression vector containing the vpu gene. Accordingly, drugs that on their own are not clinically effective against replication of the virus could be useful in combination with the U protein to enhance the attenuation effect.

The present invention is further illustrated by the following examples. These examples are provided to aid in the understanding of the invention and are not to be construed as a limitation thereof.

EXAMPLES

The ability of the vpu gene, i.e. the region between the first coding exon of tat and the env gene nucleotide sequences corresponding to a sufficient number of nucleotides from 5541-8017 of the HIV genome contain an AUG start codon, to encode a protein was examined by programming an in vitro reticulocyte translation lysate [Pelham, H. P. B., et al, Eur. J. Biochem. 67:247-256 (1986)] with RNA synthesized in vitro using the method of Melton, D. A., et al, Nucl. Acid. Res. 12:7035-7056 (1984). RNA was made from a restriction fragment 2231 nucleotides long of an HIV provirus that spanned the region between the first coding exons of the tat, art and part of the env genes. The template for the experiment was derived from a fragment of the provirus of the ELI strain of HIV-1 [Alizon, M. et al, Cell 46, supra] placed 3' to the SP6 bacteriophage RNA polymerase promoter [Melton, D. A., et al, supra]. FIG. 4 shows the SP6 plasmid used to synthesize mRNA. A BamH1 to Bgl II fragment 2231 nucleotides long from the HIV Eli provirus that spanned the region between the first coding exons of the tat, art and part of the env gene was cloned 3' to the SP6 bacteriophage RNA polymerase promoter. Internal restriction sites used to linearize the plasmids are indicated. This strain contains an open reading frame in this region that initiates with an AUG codon (FIG. 1B) [Alizon, M., et al, Cell 46, supra]. The viral sequences present in this RNA transcript, as shown in FIG. 4, extend from the 5' end of the first coding exon of the tat (Bam H1 site) to 1839 nucleotides (Bgl II site) within the env. The initiation codon for the tat gene is not intact in this RNA as the restriction enzyme used, Bam H1, cleaves the ELI proviral strain between the T and the G of the tat initiation codon.

Proteins produced in the in vitro lysate using the RNA derived from this proviral fragment were labeled with $^{35}$S-methionine and separated by size using sodium dodecyl sulfate (SDS)-polyacrylamide gel electrophoresis (PAGE). See FIG. 2A, pEU plasmid was linearized by digestion at an EcoRI site located in the polylinker 3' to the HIV$_{Eli}$ insert and used as a template for in vitro transcription by SP6 RNA polymerase as described [Pelletier, J. & Sonenberg, N., Cell 40:515-526 (1985)] except that the concentration of GTP and Cap analogue m$^7$GpppG were raised to 0.2 and 1.0 mM respectively. Messenger RNAs were labeled with [5-$^3$H] CTP and purified as described (27). In vitro translation of equimolar amounts of RNA (equal amounts of radioactivity) was performed in reticulocyte lysate [Pelham, H. P. B., et al, Eur. J. Biochem., 67:247-256 (1986)]. Incubation was done at 30° C. for 30 minutes in the presence of $^{35}$S-Methione. Labeled products were analyzed directly by 15% SDS-PAGE (lane 2) or immunoprecipitated [Lee, T. H. et al, Cell 44:941-947] beforehand with preimmune rabbit serum (lane 3); anti-peptide 2 serum (lane 4); anti-peptide 2 serum in the presence of 500 mM of peptide 2 (lane 5), peptide 1 (lane 6), or an unrelated peptide QEEAETATKTSSC (lane 7). Lane 1 represents a total translation reaction with no mRNA added. The proteins synthesized in this system are displayed in Lane 2. The proteins precipitated by rabbit anti-peptide 2 serum are also shown. Two proteins of molecular weight of approximately 15 kD and 16 kD are evident in the unfractionated extract and are precipitated by the rabbit antisera. The 15 kD and 16 kD proteins are not precipitated by the sera from preimmune rabbit sera (lane 3). All three of the antisera to peptide 2 recognize both proteins (lane 4) as do the antisera to peptide 1 albeit more weakly (data not shown). The data of FIG. 2A also show that peptide 2 competes for recognition of the 15 kD and 16 kD proteins by antisera (lane 5). However, peptide 1 (lane 6) or an unrelated peptide do not compete with anti-peptide 2 serum (lane 7).

RNA from other proviral fragments was prepared for analysis of the in vitro translation products In one set of experiments, the template used for synthesis of RNA was truncated by restriction enzyme cleavage either 7 nucleotides 5' to the proposed AUG codon (Rsa I stie) or 30 nucleotides 3' to the proposed AUG codon (Bbv I site) (see FIG. 4). No specific protein products recognized by anti-peptide 2 antiserum were observed in these experiments (FIG. 2b, lane 1 and 2). When the template used for synthesis of RNA was cleaved 102 nucleotides 3' to the proposed stop codon (NdeI site), the 15 kD and 16 kD proteins were detected using anti-peptide 2 serum (FIG. 2B) (lane 3 and 4). pEU plasmid was linearized with the following restriction enzymes RsaI (lane 1); Bbv I (lane 2) and Nde I (lanes 3 and 4). SP6 generated RNAs were translated in vitro and immunoprecipitation was performed on the labeled products using anti-peptide 2 serum (lanes 1, 2 and 4). Lane 3 represents a total in vitro translation reaction.

The sequence of the HXBc2 clone of the IIIB isolate, as aforesaid, suggests that the RNA derived from this region should be incapable of producing the proteins as it lacks an initiation codon at the 5' end of the open reading frame. RNA was prepared by in vitro transcription of the fragment of the HXBc2 proviral clone that spans the region between the first coding exons of tat and art and part of the env gene (Bam H1 site; nucleotide 8017) and corresponds to the Eli fragment present in Eu. This RNA was used to program a reticulocyte lysate in a similar manner as described above. As was the case for the ELI proviral RNA, the initiation codon of the tat was deleted from the RNA. Proteins corresponding to the 15 kD and 16 kD products were not found in either the total $^{35}$S-methionine-labelled extract or in the precipitates obtained using anti-peptide 2 serum (FIG. 2C, lane 1, 2). A plasmid (pXU) containing a Sal I (position 5441) to BamH1 (position 8017) restriction fragment from the HXBc2 Dtat-1 proviral DNA clone [Dayton, A. I., Cell 44:941-947] located 3' to the SP6 RNA polymerase promoter [Melton, D. A., et al, Nucl. Acid. Res. 12:7035-7056 (1984)] was constructed by standard techniques. pXU was linearized with EcoR1 and used as template for in vitro transcription. After in vitro translation, the labelled products were analyzed directly on 15% SDS PAGE (lane 1) or immunoprecipitated beforehand with anti-peptide 2 serum (lane 2) or an HIV-1 infected patient serum (lane 3). However, immunoprecipitation with HIV-1 infected patient serum clearly showed the presence of truncated envelope product (lane 3).

Figures 3A, 3B, 3C, 3D:
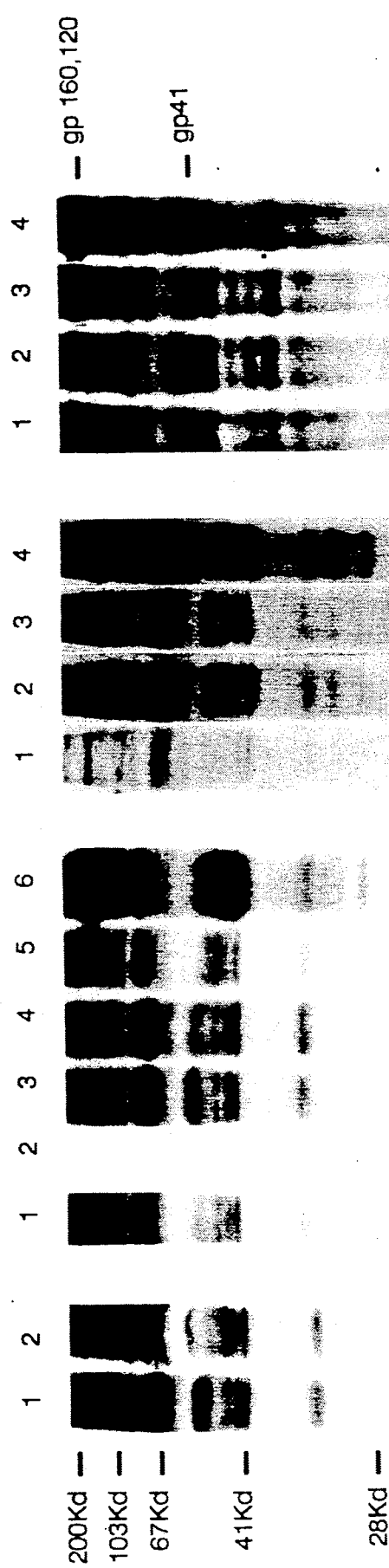
FIG. 3A-D are radiograms showing the identification of the vpu gene product in cell lines expressing constitutively proteins encoded by the 3' half of the Eli strain of HIV-1.

FIG. 2D shows the cross-reactivity between this protein and the HIV-2 and SIV viruses. After in vitro translation of SP6 generated pEU RNA, the labeled products were immunoprecipitated with normal human serum (lane 1); HIV-1 infected human serum (lane 2); HIV-1 infected patient serum in the presence of 500 mM of peptide 2 (lane 3); HIV-2 infected human serum (lane 4) or SIV-infected *Rhesus macaques* serum (lane 5). The immunoprecipitates were resolved on 15% SDS-PAGE. The ability of the anti-peptide 2 serum to recognize the 15 kD and 16 kD proteins was examined in three cell lines that express constitutively HIV-1 proteins encoded by the 3' half of the virus. [These cell lines were prepared as described in U.S. patent application Ser. Nos. 806,263 and 865,151 which are incorporated herein by reference.] Cloned HeLa cell lines that have the region between the art gene and the 3' LTR of the proviral Eli, HXBc2 and Mal strains [Alizon, M. et al, Cell 46, supra] of HIV stably integrated were constructed and then isolated using standard techniques. The parental cells used to isolate these cell lines had previously been selected for constitutive expression of the tat gene product, following infection with a retroviral vector carrying the tat coding sequences [Rosen, C. A., et al, J. Virol. 57:379-384 (1985) which is incorporated herein by reference]. Cells were labeled with [$^{35}$S] methionine and cysteine and cell lysates were immunoprecipitated as described [Lee, T. H., et al, Proc. Natl. Acad. Sci. USA 81:7579-7583 (1984)]. These cell lines constitutively produce both the art and env gene products. The plasmids used for construction of these cell lines contained the HIV LTR juxtaposed 5' to the initiation codon of the art gene. The tat gene product was supplied in trans. FIG. 3A shows HeLa tat cell line lysates immunoprecipitated with anti-peptide 2 serum (lane 1) or HIV-1 infected patient serum (lane 2). FIG. 3B shows HeLa tat Eli lysates immunoprecipitated with preimmune rabbit serum (lane 1); antipeptide 2 serum (lane 3); anti-peptide 2 serum in the presence of 500 μM of peptide 2 (lane 4); normal human serum (lane 5); HIV-1 infected patient serum (lane 6). Lane 2 represent an immunoprecipitation of labeled in vitro translated product from pEU RNA with anti-peptide 2 serum. FIG. 3C shows HeLa tat Mal lysate immunoprecipitated with preimmune rabbit serum (lane 1); anti-peptide 2 serum (lane 2); normal human serum (lane 3) and HIV-1 infected patient serum (lane 4). FIG. 3D shows HeLa tat III B lysate immunoprecipitated with preimmune rabbit serum (lane 1); anti-peptide 2 serum (lane 2); normal human serum (lane 3) and HIV-1 infected patient serum (lane 4). The data of FIG. 3 demonstrates that the anti-peptide 2 antiserum specifically recognized a 15 kD protein in the cell line derived from the Eli provirus (lane 3) that comigrates with the 15 kD protein made in vitro (lane 2). The same antiserum does not recognize a protein in the cell line that expresses proteins derived from the MAL (FIG. 3C) or the HXBc2 (FIG. 3D) proviruses. This is the predicted result as neither the HXBc2 nor Mal proviruses contain a properly positioned initiation codon (FIG. 2B). The absence of detection of the 15 kD protein by the HIV-1 patient antiserum in the cell line derived from the Eli provirus is apparently due to both the low anti-vpu titer in the patient antiserum used and the much smaller amount of the 15 kD protein in the cell line compared to the in vitro translation products.

To examine the function of the U protein on the viral life cycle, we constructed a recombinant provirus in which sequences in HXBc2 between a SalI site at position 5332 and a BamH1 site at position 8017 (+1 being the transcription initiation site) were replaced with the corresponding sequences from clone BH10.

Unlike HXBc2, BH10 possesses the AUG initiation codon for the U protein. BH10 is otherwise closely homologous to HXBc2. The net result of this recombination was to generate a proviral clone very similar to HXBc2 except for a small number of conservative amino acid changes in the tat, art and env gene products, and the ability to utilize the U open reading frame. Transfection of Jurkat cells with HXBc2 and the recombinant BH10 clones both resulted in production of virus, but spread of the BH10 derived virus through the culture was significantly slower than the spread of the HXBc2-derived virus.

Figure 5A:
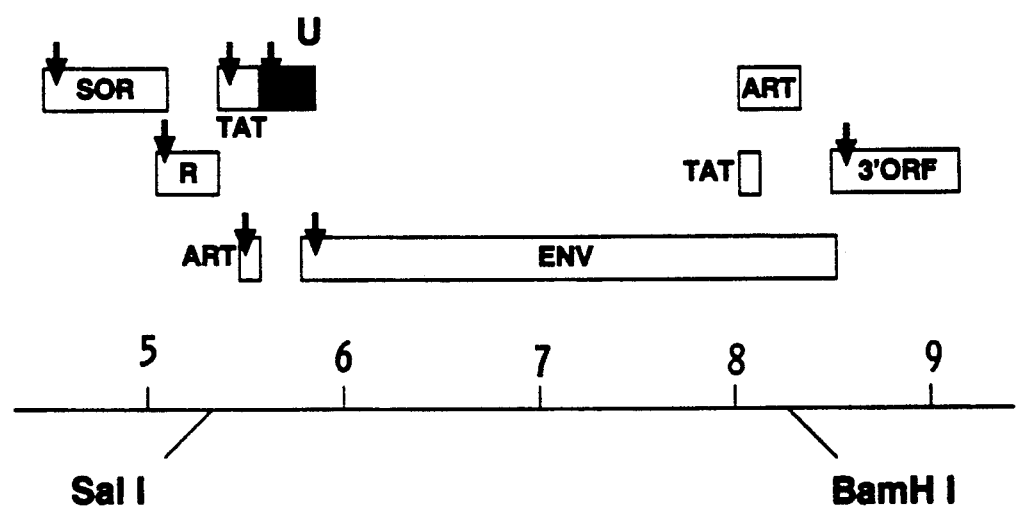
FIG. 5A is a schematic showing the recombinant provirus constructed for comparison of viruses capable of producing the vpu gene product with viruses incapable of making it.
Figure 5B:
FIG. 5B is an autoradiogram showing the differences in production of viral products resulting following transfection of lymphocytes with proviral plasmids either capable or incapable of producing the vpu gene product.

Aliquots of each culture were metabolically labelled 2, 4, and 7 days post-transfection with $^{35}$S-cystein and $^{35}$S-methionine. Extracts of the cells were then immunoprecipitated with AIDS-patient antiserum and run out on a 12.5% polyacrylamide gel. An autoradiogram of the gel is shown in FIG. 5B, Lanes 1, 4, and 7-control cells 2,4, and 7 days post-transfection, respectively; lanes 2, 5, and 8-cells transfected with HXBc2, days 2, 4, and 7, respectively; lanes 3, 6, 9-cells transfected with BH10 recombinant provirus, days 2, 4, and 7, respectively.

It is evident that those skilled in the art, given the benefit of the foregoing disclosure, may make numerous modifications thereof and departures from the specific embodiments described herein, without departing from the inventive concepts and the present invention is to be limited solely by the scope and spirit of the appended claims.

We claim:

1. A protein encoded by the entire HIV vpu gene wherein said protein has a purity that is the same as that achieved by immunoprecipitation using a rabbit antiserum which binds said protein followed by sodium dodecyl sulfate polyacrylamide gel electrophoresis.

2. The protein of claim 1, which is selected from any of the HIV vpu proteins of FIG. 1B.

3. A protein encoded by the entire HIV vpu gene in a DNA segment containing the entire HIV vpu gene but which does not contain the entire HIV-1 genome, or an antigenic fragment thereof, wherein said antigenic fragment is encoded by the portion of the HIV vpu gene coding for said fragment, wherein said protein or antigenic fragment has a purity that is the same as that achieved by immunoprecipitation using a rabbit antiserum which binds said protein followed by sodium dodecyl sulfate polyacrylamide gel electrophoresis.

4. The protein of claim 3, which is selected from any of the HIV vpu proteins of FIG. 1B.

5. The antigenic fragment of claim 3, which is a portion of any of the HIV vpu proteins of FIG. 1B.

6. The antigenic fragment of claim 5, which is peptide 1 or peptide 2 of any of the HIV vpu proteins of FIG. 1B.

7. The antigenic fragment of claim 3 comprising the amino acid sequence $X^1APWDX^2DDL$, wherein $X^1$ is H, D or L and $X^2$ is I or V.

8. The antigenic fragment of claim 7, wherein $X^1$ is H.

9. The antigenic fragment of claim 7, wherein $X^2$ is I.

10. The antigenic fragment of claim 8, wherein $X^2$ is I.

11. The protein of claim 3 wherein the protein has molecular weight of about 16 kD.

12. The protein of claim 3, wherein the protein has molecular weight of about 15 kD.

13. The protein of claim 11, which is cleaved to form a 15 kD protein.

14. A method of assay for the presence of antibody raised against HIV viral protein U, which comprises:
   (a) taking a biological specimen;
   (b) adding the protein or antigenic fragment of claim 3 to the biological specimen for a time and under conditions sufficient for the protein or antigenic fragment to bind to antibody in said biological specimen; and
   (c) determining whether an antibody-antigen complex is formed with the protein or antigenic fragment, wherein formation of said complex is indicative of the presence of said antibody.

15. A method of assay for the presence of HIV viral protein U, which comprises:
   (a) taking a biological specimen;
   (b) adding an antibody raised against the protein or antigenic fragment of claim 3 to the biological specimen for a time and under conditions sufficient for the antibody to bind to the HIV viral protein U in said biological specimen; and
   (c) determining whether an antibody-antigen complex is formed with the protein or antigenic fragment, wherein formation of said complex is indicative of the presence of HIV viral protein U.

* * * * *

UNITED STATES PATENT AND TRADEMARK OFFICE
CERTIFICATE OF CORRECTION

PATENT NO. : 5,043,262
DATED : 8/27/91
INVENTOR(S) : W.A. Haseltine, E. Terwilliger and E. Cohen It is certified that error appears in the above-identified patent and that said Letters Patent is hereby corrected as shown below:

At column 1, line 6, before "The", insert the following paragraph:

--This invention was made with government support under Grant No. AI28193 awarded by the National Institutes of Health. The government has certain rights in the invention.--

Signed and Sealed this

Twenty-fourth Day of January, 1995

Attest:

BRUCE LEHMAN

Attesting Officer     Commissioner of Patents and Trademarks